(12) United States Patent
Twigg

(10) Patent No.: US 9,101,879 B2
(45) Date of Patent: Aug. 11, 2015

(54) CATALYSTS

(75) Inventor: Martyn Vincent Twigg, Cambridge (GB)

(73) Assignee: JOHNSON MATTHEY PLC, London (GB)

( * ) Notice: Subject to any disclaimer, the term of this patent is extended or adjusted under 35 U.S.C. 154(b) by 1097 days.

(21) Appl. No.: 13/139,132

(22) PCT Filed: Dec. 10, 2009

(86) PCT No.: PCT/GB2009/051686
§ 371 (c)(1),
(2), (4) Date: Aug. 26, 2011

(87) PCT Pub. No.: WO2010/067120
PCT Pub. Date: Jun. 17, 2010

(65) Prior Publication Data
US 2011/0300018 A1    Dec. 8, 2011

(30) Foreign Application Priority Data
Dec. 10, 2008   (GB) .................................. 0822479.2

(51) Int. Cl.
| | | |
|---|---|---|
| *B01J 21/06* | (2006.01) | |
| *B01J 21/08* | (2006.01) | |
| *B01J 23/34* | (2006.01) | |
| *B01J 23/50* | (2006.01) | |
| *B01D 53/02* | (2006.01) | |
| *B01D 53/14* | (2006.01) | |
| *B01D 53/66* | (2006.01) | |
| *B01D 53/86* | (2006.01) | |
| *B01J 23/68* | (2006.01) | |
| *B01J 23/96* | (2006.01) | |
| *B01J 35/02* | (2006.01) | |
| *B01J 35/04* | (2006.01) | |
| *B01J 37/02* | (2006.01) | |
| *A61L 2/20* | (2006.01) | |
| *B01J 23/42* | (2006.01) | |

(52) U.S. Cl.
CPC ............. *B01D 53/8675* (2013.01); *B01J 23/50* (2013.01); *B01J 23/688* (2013.01); *B01J 23/96* (2013.01); *B01J 35/023* (2013.01); *B01J 35/04* (2013.01); *B01J 37/0215* (2013.01); *A61L 2/202* (2013.01); *A61L 2202/13* (2013.01); *B01D 2255/104* (2013.01); *B01D 2255/2073* (2013.01); *B01D 2255/20707* (2013.01); *B01D 2255/30* (2013.01); *B01J 21/063* (2013.01); *B01J 21/08* (2013.01); *B01J 23/34* (2013.01); *B01J 23/42* (2013.01)

(58) Field of Classification Search
USPC .................. 502/243, 324, 344, 347; 423/219, 423/240 R, 242.1, 244.01, 244.02; 422/30
IPC .......... B01J 21/06,21/063, 21/08, 23/34, 23/50, B01J 23/688; B01D 53/02, 53/14, 53/66
See application file for complete search history.

(56) References Cited

U.S. PATENT DOCUMENTS

| | | | | |
|---|---|---|---|---|
| 2,203,188 | A * | 6/1940 | Beer ................................ | 422/4 |
| 4,379,129 | A * | 4/1983 | Abe .............................. | 423/219 |
| 4,871,709 | A * | 10/1989 | Tatsushima et al. .......... | 502/324 |
| 5,002,920 | A * | 3/1991 | Yoshimoto et al. ........... | 502/324 |
| 5,080,882 | A * | 1/1992 | Yoshimoto et al. ........... | 423/579 |
| 5,192,452 | A | 3/1993 | Mitsui et al. | |
| 5,214,014 | A * | 5/1993 | Yoshimoto et al. ............. | 502/84 |
| 5,221,649 | A | 6/1993 | Yoshimoto et al. | |
| 5,472,676 | A | 12/1995 | Terui et al. | |
| 6,683,024 | B1* | 1/2004 | Khare et al. .................. | 502/400 |
| 2005/0214186 | A1* | 9/2005 | Michalakos et al. .......... | 423/219 |
| 2008/0283446 | A1 | 11/2008 | Tatarchuk et al. | |
| 2010/0021360 | A1* | 1/2010 | Leenders et al. .............. | 423/219 |

FOREIGN PATENT DOCUMENTS

| | | |
|---|---|---|
| EP | 0 275 620 A2 | 7/1988 |
| EP | 0 361 385 A2 | 4/1990 |
| EP | 0 367 574 A2 | 5/1990 |
| JP | 62-97643 A | 5/1987 |
| JP | 471644 A | 3/1992 |
| JP | 549863 A | 3/1993 |
| WO | WO-2005/087278 A1 | 9/2005 |
| WO | WO-2005/097303 A1 | 10/2005 |

OTHER PUBLICATIONS

Wang et al., "Propylene epoxidation over silver supported titanium silicalite zeolite," *Catalysis Letters*, vol. 90, Nos. 1-2, Sep. 2003, pp. 57-63.
Linke et al., "Synthesis and Crystal Structure of Disilvertitanate-(IV), $Ag_2TiO_3$," *Journal of Solid State Chemistry*, vol. 134, 1997, pp. 17-21.
International Search Report dated Jun. 18, 2010, issued in International Application No. PCT/GB2009/051686.
British Search Report dated Apr. 8, 2009, issued in British Patent Application No. 0822479.2.

\* cited by examiner

*Primary Examiner* — Patricia L Hailey
(74) *Attorney, Agent, or Firm* — Young & Thompson

(57) ABSTRACT

A sterilant such as ozone used for large scale decontamination of, for example, a hospital room, may be destroyed and the room made safe, by passing the atmosphere in the room over a catalyst which is silver oxide in combination with titania. The catalyst may be readily regenerated and used again.

16 Claims, No Drawings

CATALYSTS

CROSS-REFERNECE TO RELATED APPLICATION

This application is the U.S. National Phase application of PCT Internantional Application No.PCT/GB2009/051686, filed Dec. 10, 2009, and claims priority of British Patent Application No. 0822479.2, filed Dec. 10, 2008, the disclosures of both of which are incorporated herein by reference in their entirety for all purposes.

FIELD OF THE INVENTION

The present invention concerns improvements in catalysts, and more especially concerns supported silver oxide catalysts. Such catalysts may be used in the destruction of excess sterilants such as ozone or hydrogen peroxide.

BACKGROUND TO THE INVENTION

The use of a sterilant such as ozone or hydrogen peroxide is established for removing many bacteria and other pathogenic microorganisms from an enclosed area environment. Unfortunately, such sterilants are also toxic or hazardous to higher life forms such as humans or domesticated animals, and great care has to be taken to reduce the concentration of the sterilant to safe levels before allowing access.

Contaminants to be removed may be of biological or of synthetic origin, including bacterial, viral, and other pathogens, or synthetic toxic agents such as compounds that interfere with biological processes. The environments may include areas where plants are grown such as greenhouses, food processing areas such as kitchens, hotel rooms, conference centres, isolation rooms and other areas in hospitals etc that may have been contaminated as well as rooms in dwellings and ambulances etc, and places where animals are kept such as on farms and zoos, especially quarantine areas, but including henhouses or other areas of high concentrations of animals.

Decontamination equipment to be used may be fixed or portable with electrical power from the mains supply, or from internal rechargeable batteries that are periodically recharged.

For ease of description, the following description concentrates on the use of ozone as the sterilant.

It is generally known that it may be advantageous to humidify the atmosphere prior to or during sterilisation. Humidification of the air may be achieved by spaying a mist of water droplets from a suitable nozzle(s), or by passing steam into the environment that would normally be at a temperature between 10° C. and 45° C., before, at the same time, or subsequent to introducing ozone into the environment. It is believed that the higher the humidity the better—the water enhances the effectiveness of the ozone, perhaps through formation of hydroxyl radicals that are especially potent oxidants, but this may depend on the actual prevailing conditions. At present, it is envisaged that humidification to greater than about 70% relative humidity will be preferred, but other humidity levels may be used.

As indicated above, the ozone may react with water vapour to form hydroxyl radicals, a particularly powerful oxidant, and it is probable that it is hydroxyl radicals that are the highly active agent. Combination of hydroxyl radicals in three body reactions would lead to formation of hydrogen peroxide that also has powerful antiseptic properties.

Ozone may be produced from a suitable ozone generator such as irradiating oxygen with ultraviolet irradiation or electrical techniques such as those involving corona discharge or plasma formation. Preferably the source of oxygen contains only limited amounts of nitrogen (eg less than 15%) to minimise the formation of undesirable nitrogen oxides. Although air may be used as the source of ozone, it is preferred to use pure oxygen or oxygen-enriched air.

The amount of ozone in the environment should be maintained at a level and time sufficient to destroy all of the contaminants present. Typical values are at least 10-50 ppm ozone and preferably 20-40 ppm ozone for 20-120 minutes, and preferably 30-60 minutes.

After the ozone and its derivatives have decontaminated the environment, the atmosphere of the environment is suitably circulated using a fan through a filter to remove particulate matter that might be present, and then over a catalyst to convert remaining ozone and its derivatives, such as hydrogen peroxide, to oxygen, or oxygen and water, so that the environment is safe for human or animal occupation.

The procedure described above may be accomplished using a computer-controlled system—for maintaining humidification, ozone levels for predetermined periods, and thereafter switching these off, and generating a flow of the atmosphere through a special catalyst to reduce the ozone to a safe level. Sensors provide inputs for this control, and predictive computer models enable reliable estimates to be made of the times needed for decontamination and the times needed to reduce the ozone to safe levels.

The prior art indicates active ozone decomposition catalysts include formulations containing metal components such as platinum or oxides such as those of manganese and other transition metal elements. Surprisingly, we have found platinum catalysts do not work well in this application involving high ozone levels and high humidity levels at ambient temperatures. Moderately good initial performance was observed but deactivation was very rapid. This may be due to strong adsorption of water and/or oxygen species on the active sites, and highlights the fact that this ozone-destruction application is very demanding. Highly-loaded $MnO_2$ catalysts had good initial activity, and while initially better than platinum, they quickly deactivated in use. We found removal of adsorbed species by vacuum oven treatment overnight at 150° C. restored a portion of the lost activity, but the combination of rapid deactivation and slow regeneration clearly means that this catalyst is certainly not a practical solution.

Some prior art suggests silver oxide/$MnO_2$ catalysts can have very good ozone decomposition activity. Silver oxide/$MnO_2$ catalysts were prepared and tested, but again they deactivated quickly under the unusual conditions of very high humidity and very high ozone concentrations at low temperature. It was thought humidity in particular was responsible for catalyst deactivation, and there was some experimental evidence to support this.

SUMMARY OF THE INVENTION

We have found that the presence of low levels of promoters has a major influence on catalytic performance of silver oxide catalysts in the present application. Through an optimisation process, it was discovered that silver oxide catalyst formulations containing alumina had relatively poor initial performance and after only a little use they lost considerable activity. Silver oxide with silica performed better, but silver oxide with silica and titania performed surprisingly well and surprisingly maintained this performance over extended duty cycles. It appears that silver oxide with titania has improved activity compared to silica/titania supports.

Accordingly, in a first aspect the present invention provides a catalyst for the destruction of ozone or other sterilant, comprising silver oxide, titania and optionally $MnO_2$ in an amount of up to 10% by weight of the catalyst.

In a second aspect, the present invention provides a method for removal of ozone or other sterilant from an atmosphere, comprising passing the atmosphere over a catalyst comprising silver oxide, titania and optionally $MnO_2$ in an amount of up to 10% by weight of the catalyst.

In a third aspect, the present invention provides a method of sterilising an enclosed space, comprising humidifying the atmosphere in the space and subsequently or simultaneously supplying an amount of ozone or other sterilant that achieves sterilisation in a predetermined period, then subsequently catalytically destroying the sterilant by passing the atmosphere over a catalyst comprising silver oxide, titania and optionally $MnO_2$ in an amount of up to 10% by weight of the catalyst.

DETAILED DESCRIPTION OF THE INVENTION

As noted above, the catalyst comprises silver oxide and titania but may also include small amounts of manganese dioxide. If manganese dioxide is present, it will not amount to more than 10% by weight of the catalyst. The catalyst may also include small amounts of silica, typically up to 15% by weight of the catalyst.

The proportion of silver oxide to titania and other oxides if present may be determined by conventional optimisation techniques but preferably the catalyst comprises at least 60% by weight of silver oxide, more preferably at least 70%, even more preferably at least 80% by weight of silver oxide.

The catalyst may be prepared using known technology and may be supported on conventional honeycomb monoliths having parallel channels, of the flow-through type, made from for example, ceramic or suitable stainless steel materials. The coating of supports using washcoats comprising the catalytically active component(s) and particulate supports is well established. In our preliminary tests on flow-through ceramic honeycomb supports, washcoat loadings of about 1.5 to 2.5 g/cu in have been used. Specific catalyst manufacturing techniques and washcoat/catalyst loadings may be optimised for particular applications in conventional manner.

With supported catalysts, low pressure-drop is important because of fan size limitations in practical application, especially with portable equipment. The flow through catalyst is normally housed in a metal (e.g. stainless steel) cylinder retained with a ceramic mat material, and having suitable coupling devices at its ends. Such arrangements are well known for vehicle catalytic converters.

The catalyst may be supported on a wall-flow filter in which alternate channel ends are plugged so forcing the gas to flow through the filter walls. The catalyst may be deposited on and/or in the filter walls thereby making more effective use of the catalyst at the expensive of increased backpressure. Foamed or pellet catalyst types can also be used in a suitable container preferable made from stainless steel or other ozone resistant material. Alternative supports such as high surface area sintered metal monoliths, metal devices known as static mixers, and partial filter constructions, may be used if appropriate.

Having a small amount of silica present as a binder in a washcoat is generally expected to improve washcoat adhesion to flow-through or filter-type supports, although we have not encountered adhesion problems with any of the catalysts we have prepared.

Silver containing catalysts can be susceptible to poisoning, especially at low temperature, particularly by sulphur compounds in either low or high oxidation state eg $H_2S$ and $SO_2$. Because of the very large volumes of air passed over these catalysts in a working system, even small amounts of poison can rapidly cause at least some deactivation. It is therefore proposed that catalyst life is extended by protecting it with an upstream small volume of guard material that has a high affinity for poisons. Such guard material may be two separate layers or mixtures of high surface area zinc oxide (for $H_2S$) and a form of alkalised high surface area material, such as alkalised alumina, to capture halides. The guard materials could be in the form of pellets or other solid form in a suitable container or alternatively coated onto a flow-through ceramic or metal monolithic honeycomb.

Our working examples described herein all use single catalyst supports 10.5 inch diameter and 6 inches long (approx 26.67 cm by 15.24 cm) (400 cpsi, 6 mil channel walls)—but this was for convenience and it is expected that other catalyst supports will be effective. Multiple smaller catalysts in parallel could provide greater flexibility, for example each catalyst could be fitted with its own fan and switching these on sequentially saves the cost of having soft start motor procedures etc. Other standard diameters of catalyst supports as well as oval shapes may be considered. As suggested each might have their own fan—this could provide greater flexibility for air flow directions etc as well as being more economic.

Indications are that the catalysts of the invention are effective over higher space velocity ranges than are commonly used, meaning that an enclosed space may be made safe more quickly. Conventional air flow rates with existing commercial equipment are in the range 650-750 $m^3$/hr, equivalent to catalyst space velocities of 77-89×$10^3$ $hr^{-1}$. Our initial tests varied air flow rates from 400 to 1800 $m^3$/hr, corresponding to catalyst space velocities of 47 to 213×$10^3$ $hr^{-1}$. Ozone levels in the rooms used in the tests fell more rapidly, in proportion, with increasing space velocity.

Further research work has established that operation of the catalysts of the invention at relatively low temperatures and relatively high humidities causes the formation of silver species having an oxidation state greater than one. This has been confirmed by X-ray diffraction studies. A reduction of the used catalyst with hydrogen in nitrogen at room temperature did reduce the higher oxidation state material, but the amount of $Ag^I$ oxide did not increase, and the activity was not restored.

We have now discovered that higher oxidation state silver material in used catalyst can be effectively regenerated by heat treatment in air at moderate temperatures. For example, heating in air at 150° C. converted all or substantially all of the higher oxidation state material into the active $Ag^I$ oxide form. The catalyst may be regenerated in situ or in a dedicated apparatus.

Deactivation could be avoided by operating the catalyst at higher temperatures, e.g. at 200° C., but this is not generally practicable when decontaminating a room in a hospital, for example.

Accordingly, it is preferred to incorporate an electric heater upstream of the catalyst, which may be periodically energised to increase the temperature of the air flowing over the catalyst while reducing the flow rate. Suitable temperatures for regeneration are in the range 130-250° C., for a period of from 5 mins to 10 hours, conveniently for 15 mins to 5 hours. An advantageous regeneration regime could be to regenerate the catalyst relatively frequently for short periods, so that the catalyst maintains its performance over extended periods of time.

The invention will now be further illustrated by reference to the following examples.

CATALYST EXAMPLES

Preparation of Catalyst A. Pt/Al$_2$O$_3$ (Comparative)

Dispersible alumina (1250 g) was dispersed in deionised water (3.5 litres) adjusted to pH 4 by addition of dilute nitric acid by stirring with a high sheer mixer. The dispersed mixture was ball milled using ceria/zirconia balls for 30 minutes to give a d$_{50}$ particle size of less than 5 microns, then hydroxyethylcellulose (Natrosol from Aqualon) (6.5 g) was added during continued stirring to give a coating mixture that was easily applied to a cordierite monolithic honeycomb 10.5 inches diameter 6 inches high having 400 square channels per square inch with wall thickness of 6/1000 inch. Excess washcoat was removed with a high pressure air gun before drying in flowing air at 90° C. for 45 minutes. The washcoated monolithic honeycomb was calcined in air at 500° C. for 1 hour after which the weight of alumina on the monolithic honeycomb was 1145 g. The calcined honeycomb was impregnated with an aqueous solution containing platinum nitrate (9.6 g platinum/litre) and citric acid (100 g/litre), dried in an air flow at 90° C. before it was calcined at 500° C. for 2 hours. The coated monolith contained 12.0 g platinum.

Preparation of Catalyst D MnO$_2$/Al$_2$O$_3$ (Comparative)

Manganese dioxide was prepared by mixing hot (65° C.) aqueous solutions of KMnO$_4$ (210 g in 4 litres of water) and MnSO$_4$ (300 g in 6 litres of water) the resulting dark brown precipitate that formed was stirred at 65° C. for a further 3 hours. The precipitate was then filtered off, washed with warm deionised water (3×1 litre), and dried in an oven overnight at 110° C. to give an active form of MnO$_2$ (245 g). This preparation was repeated as necessary to provide the amounts of MnO$_2$ required. Subsequently it was found MnO$_2$ purchased from Alfa Aesar as activated manganese(IV) oxide could be substituted with similar results. To deionised water (1.2 litre) was added with stirring in a high shear mixer, MnO$_2$ (900 g) and dispersible Al$_2$O$_3$ (100 g) to give a well mixed uniform slurry. This was then ball milled using ceria/zirconia balls for 3 hours to give a d$_{50}$ particle size of less than 5 microns. Deionised water was then added and hydroxyethylcellulose (Natrosol from Aqualon) (20.2 g) to form a coating mixture that could easily be applied to a cordierite honeycomb 10.5 inches diameter 6 inches high having 400 square channels per square inch with wall thickness of 6/1000 inch. Excess washcoat was removed by a high pressure air gun, and after drying in a flow of air at 90° C. for 1 hour the resulting coated monolith had 901 g of washcoat.

Preparation of Catalyst E MnO$_2$/Al$_2$O$_3$ (Comparative)

Manganese dioxide purchased from Alfa Aesar as activated manganese(IV) oxide (1039 g) was added to deionised water (1.2 litre) with stirring in a high shear mixer, and dispersible Al$_2$O$_3$ (104 g) to give a well mixed uniform slurry. This was then ball milled using ceria/zirconia balls for 3 hours to give a d$_{50}$ particle size of less than 5 microns. Deionised water was then added and hydroxyethylcellulose (Natrosol from Aqualon) (6.7 g) to form a coating mixture that could easily be applied to a cordierite honeycomb 10.5 inches diameter 6 inches high having 400 square channels per square inch with wall thickness of 6/1000 inch. Excess washcoat was removed by a high pressure air gun, and after drying in a flow of air at 90° C. for 1 hour the resulting coated monolith had 1030 g of washcoat.

Preparation of Catalyst F Ag$_2$O/MnO$_2$/TiO$_2$/SiO$_2$ (Comparative)

To deionised water (1.2 litre) was added with stirring in a high shear mixer, silver oxide (441 g), MnO$_2$ (441 g), TiO$_2$ (156 g) and SiO$_2$ (104 g) to give a well mixed uniform slurry. This was then ball milled using ceria/zirconia balls for 3 hours to give a d$_{50}$ particle size of less than 5 microns. Deionised water was then added and a xanthan gum, Rhodapol from Rhone-Poulenc SA (20.2 g) was added to give a coating mixture with properties enabling easy application to a cordierite honeycomb 10.5 inches diameter 6 inches high having 400 square channels per square inch with wall thickness of 6/1000 inch. Excess washcoat was removed by a high pressure air gun, and after drying in a flow of air at 90° C. for 1 hour the resulting coated monolith had 1017 g of washcoat.

Preparation of Catalyst G MnO$_2$/Ag$_2$O/TiO$_2$/SiO$_2$ (Comparative)

To deionised water (1.2 litre) was added with stirring with a high shear mixer, silver oxide (707 g), MnO$_2$ (177 g), TiO$_2$ (156 g) and SiO$_2$ (104 g) to give a well mixed uniform slurry. This was then ball milled using ceria/zirconia balls for 3 hours to give a d$_{50}$ particle size of less than 5 microns. Deionised water was then added and a xanthan gum, Rhodapol from Rhone-Poulenc SA (20.2 g) was added to give a coating mixture with properties enabling easy application to a cordierite honeycomb 10.5 inches diameter 6 inches high having 400 square channels per square inch with wall thickness of 6/1000 inch. Excess washcoat was removed by a high pressure air gun, and after drying in a flow of air at 90° C. for 1 hour the resulting coated monolith had 1109 g of washcoat.

Preparation of Catalyst H. MnO$_2$/Ag$_2$O/TiO$_2$/SiO$_2$

To deionised water (1.2 litre) was added with stirring with a high shear mixer, silver oxide (960 g), MnO$_2$ (25 g), TiO$_2$ (156 g) and SiO$_2$ (104 g) to give a well mixed uniform slurry. This was then ball milled using ceria/zirconia balls for 3 hours to give a d$_{50}$ particle size of less than 5 microns. Deionised water was then added and a xanthan gum, Rhodapol from Rhone-Poulenc SA (20.2 g), to give a coating mixture with properties enabling easy application to a cordierite honeycomb 10.5 inches diameter 6 inches high having 400 square channels per square inch with wall thickness of 6/1000 inch. Excess washcoat was removed by a high pressure air gun, and after drying in a flow of air at 90° C. for 1 hour the resulting coated monolith had 1208 g of washcoat.

Preparation of Catalyst I Ag$_2$O/TiO$_2$/SiO$_2$

To deionised water (1.2 litre) was added with stirring with a high shear mixer, silver oxide (986 g), TiO$_2$ (156 g) and SiO$_2$ (104 g) to give a well mixed uniform slurry. This was then ball milled using ceria/zirconia balls for 3 hours to give a d$_{50}$ particle size of less than 5 microns. Deionised water was then added and a xanthan gum, Rhodapol from Rhone-Poulenc SA (20.2 g) was added to give a coating mixture with properties enabling easy application to a cordierite honeycomb 10.5 inches diameter 6 inches high having 400 square channels per square inch with wall thickness of 6/1000 inch. Excess washcoat was removed by a high pressure air gun, and after drying in a flow of air at 90° C. for 1 hour the resulting coated monolith had 1147 g of washcoat.

Preparation of Catalyst J $Ag_2O/SiO_2$ (Comparative)

To deionised water (1.2 litre) was added with stirring in a high shear mixer, silver oxide (986 g) and $SiO_2$ (260 g) to give a well mixed uniform slurry. This was then ball milled using ceria/zirconia balls for 3 hours to give a $d_{50}$ particle size of less than 5 microns. Deionised water was then added and a xanthan gum, Rhodapol from Rhone-Poulenc SA (20.2 g), to give a coating mixture with properties enabling easy application to a cordierite honeycomb 10.5 inches diameter 6 inches high having 400 square channels per square inch with wall thickness of 6/1000 inch. Excess washcoat was removed by a high pressure air gun, and after drying in a flow of air at 90° C. for 1 hour the resulting coated monolith had 1205 g of washcoat.

Preparation of Catalyst K $Ag_2O/Al_2O_3$ (Comparative)

To deionised water (1.2 litre) was added with stirring in a high shear mixer commercial silver oxide (Johnson Matthey) (986 g) and dispersible $Al_2O_3$ (260 g) to give a well mixed uniform slurry. This was then ball milled using ceria/zirconia balls for 3 hours to give a $d_{50}$ particle size of less than 5 microns. Deionised water was then added and a xanthan gum, Rhodapol from Rhone-Poulenc SA (26.9 g), to give a coating mixture with rheological properties enabling easy application to a cordierite honeycomb 10.5 inches diameter 6 inches high having 400 square channels per square inch with wall thickness of 6/1000 inch. Excess washcoat was removed by a high pressure air gun, and after drying in a flow of air at 90° C. for 1 hour the resulting coated monolith had 1185 g of washcoat.

Preparation of Catalyst L $Ag_2O/TiO_2$

To deionised water (1.2 litre) was added with stirring with a high shear mixer, silver oxide (986 g) and $TiO_2$ (Millennium Inorganic Chemicals) (260 g) to give a well mixed uniform slurry. This was then ball milled using ceria/zirconia balls for 3 hours to give a $d_{50}$ particle size of less than 5 microns. Deionised water was then added and a xanthan gum, Rhodapol from Rhone-Poulenc SA (20.2 g), was added with stirring to give a coating mixture with properties enabling easy application to a cordierite honeycomb 10.5 inches diameter 6 inches high having 400 square channels per square inch with wall thickness of 6/1000 inch. Excess washcoat was removed by a high pressure air gun, and after drying in a flow of air at 90° C. for 1 hour the resulting coated monolith had 1143 g of washcoat.

Test Procedure

A room, typical of a patient isolation room in a hospital, having a volume of 72 cubic metres was humidified to a predetermined relative humidity level by atomising deionised water through three nozzles arranged 120° with respect to each other in a unit about 1 metre high in the centre of the room. Ozone derived from a cylinder of pure oxygen using a plasma ozone generator manufactured by Pacific Ozone Technology was released into the room at a rate that maintained a predetermined level in the room. A computer system taking measurements from ozone and relative humidity sensors placed in the room maintained both humidity and ozone level at the desired levels in the room for at least 30 minutes. The ozone generator was then switched off and the humidification ceased via the computer control system.

The control system then circulated the air in the room through an ozone decomposition catalyst to remove the excess ozone present in the room, by use of a suitable fan. The air flow through the catalyst and the concentration of ozone was measured by sensors and data logged by computer.

Results

The decay curve of ozone concentration in the room as a function of time obeyed an exponential decay. It was a well behaved first order process. For a catalyst that suffers insignificant or predicable deactivation this relationship enables precise calculation of the time required to achieve a particular level of residual ozone in the environment given the first order decomposition rate constant under specific conditions such air flow rate through the catalyst, temperature etc. Deactivation coefficients can be applied to these calculations for field use in computer controlled systems in hospitals etc.

A synopsis of data obtained for different catalyst types in the 72 cubic metre room is given in Table 1.

TABLE 1

Summary of Test Results

| Catalyst | Run | Temp | RH | Air Flow Rate | constant | Half life | PLC |
|---|---|---|---|---|---|---|---|
| A | 01 | 17.5° C. | 89% | 671 m³/h | $1.14 \times 10^{-3}$ s$^{-1}$ | 10.1 min | |
| | 03 | 18.1° C. | 89% | 826 m³/h | $0.59 \times 10^{-3}$ s$^{-1}$ | 19.5 min | 3.13 |
| D | 01 | 19.0° C. | 70% | 677 m³/h | $3.60 \times 10^{-3}$ s$^{-1}$ | 3.21 min | |
| | 07 | 18.4° C. | 63% | 714 m³/h | $0.78 \times 10^{-3}$ s$^{-1}$ | 14.9 min | 1.67 |
| E | 01 | 19.8° C. | 47% | 705 m³/h | $3.81 \times 10^{-3}$ s$^{-1}$ | 3.04 min | |
| | 06 | 21.0° C. | 43% | 705 m³/h | $1.24 \times 10^{-3}$ s$^{-1}$ | 9.32 min | 1.05 |
| F | 01 | 24.0° C. | 42% | 671 m³/h | $3.41 \times 10^{-3}$ s$^{-1}$ | 3.41 min | |
| | 09 | 23.1° C. | 89% | 671 m³/h | $1.58 \times 10^{-3}$ s$^{-1}$ | 7.31 min | 0.43 |
| G | 01 | 22.0° C. | 75% | 683 m³/h | $3.59 \times 10^{-3}$ s$^{-1}$ | 3.22 min | |
| | 12 | 17.0° C. | 89% | 677 m³/h | $2.28 \times 10^{-3}$ s$^{-1}$ | 5.07 min | 0.15 |
| H | 01 | 18.3° C. | 89% | 661 m³/h | $3.18 \times 10^{-3}$ s$^{-1}$ | 3.63 min | |
| | 18 | 19.9° C. | 84% | 707 m³/h | $3.10 \times 10^{-3}$ s$^{-1}$ | 3.73 min | 0.006 |
| I | 01 | 21.0° C. | 85% | 657 m³/h | $2.91 \times 10^{-3}$ s$^{-1}$ | 3.96 min | |
| | 32 | 20.0° C. | 88% | 685 m³/h | $3.14 \times 10^{-3}$ s$^{-1}$ | 3.68 min | 0.007 |
| J | 01 | 17.0° C. | 82% | 691 m³/h | $1.31 \times 10^{-3}$ s$^{-1}$ | 8.80 min | |
| | 02 | 17.2° C. | 83% | 691 m³/h | $1.35 \times 10^{-3}$ s$^{-1}$ | 8.51 min | −0.15 |
| K | 01 | 15.0° C. | 84% | 683 m³/h | $2.75 \times 10^{-3}$ s$^{-1}$ | 4.20 min | |
| | 02 | 16.0° C. | 85% | 683 m³/h | $2.73 \times 10^{-3}$ s$^{-1}$ | 4.23 min | 0.015 |

TABLE 1-continued

Summary of Test Results

| Catalyst | Run | Temp | RH | Air Flow Rate | constant | Half life | PLC |
|---|---|---|---|---|---|---|---|
| L | 01 | 17.5° C. | 83% | 685 m$^3$/h | 3.69 × 10−3 s$^{-1}$ | 3.13 min | |
| | 04 | 18.0° C. | 80% | 685 m$^3$/h | 3.47 × 10−3 s$^{-1}$ | 3.33 min | |
| | 07 | 17.6° C. | 86% | 685 m$^3$/h | 3.85 × 10−3 s$^{-1}$ | 3.00 min | −0.019 |

We defined a Performance and Longevity Coefficient (PLC) to give an approximate rank to catalysts in this application, PLC=(half-life after N duty cycles−initial half-life)/N. In general the lower the value of the PLC the better is the catalyst, though if the initial performance is inadequate its PLC is irrelevant.

Surprisingly a variety of established ozone decomposition catalysts lost activity very quickly, and this was thought to be due to the very unusually demanding conditions of very high ozone and humidity levels at room temperature which is a relatively low temperature in terms of a catalysed process.

The catalysts of the invention achieved greater than the very high 99.4% conversion of ozone necessary to reduce the level of ozone to levels that are accepted as safe for human exposure surprisingly quickly without any noticeable loss of performance over many use/regeneration cycles.

Comments on the Results

1. Catalyst A

Initial work with a platinum catalyst (6 inch long, 40 g/ft$^3$) showed it had an initial half life of a little more than 10 minutes, but after three experiments this increased to 19.5 minutes even with a significantly higher air flow rate over the catalyst. This was not very much better than the half-life for the natural decay of the ozone in the room that was typically 20.7 minutes. It was therefore concluded the performance of platinum catalyst was inadequate for the application because platinum catalysts did not perform well initially and they rapidly lost activity.

2. Catalysts D and E

Preliminary work on manganese oxide/alumina catalysts showed they performed very much better than Catalyst A, having initial half-lives of about 3 minutes. However durability was not acceptable, the half-life for Catalyst D was about 15 minutes after 7 experiments. The high humidity was shown to be an important factor here—compare half-lives for Catalysts D and E run at different humidities. The lower the humidity the longer the catalyst life, and dehydrating a used catalyst improved its performance.

3. Catalysts F, G, and H

Addition of silver oxide to a manganese oxide catalyst containing titania and silica improved performance in proportion to the amount of silver oxide present and in inverse proportion to the amount of manganese dioxide present. In particular Catalyst H with the highest silver oxide content and lowest manganese dioxide content of these three catalysts had by far the best half-life obtained at the time of testing—3.7 minutes after 18 runs.

4. Catalyst I

This catalyst contained a large proportion of silver oxide with silica and titania and no manganese oxide. Performance was very good indeed, maintaining good activity up to 32 runs when the half life was 3.7 minutes.

5. Catalysts J, K and L

These catalysts were prepared to probe the effect of having just single additions of alumina, silica and titania in silver oxide containing catalysts. Catalyst J had a poor performance (initial half-life 8.8 minutes) showing alumina had a poor influence on the performance of silver oxide in ozone decomposition. Catalyst K had fairly good, though not outstanding performance with an initial half-life of 4.2 minutes. However, Catalyst L containing silver oxide with titania had a very good half-life of 3.1 minutes with good durability.

Example of Catalyst Regeneration

At present, it appears that the two best catalysts investigated are Catalyst I (silver oxide/titania/silica) and Catalyst L (silver oxide/titania); both are being investigated further.

The X-ray diffraction pattern of used, poorly performing catalyst I contained only low intensity reflections characteristic of Ag$^I_2$O with the dominant silver phase being the mixed oxidation state species A$^I$Ag$^{III}$O$_2$. It was found heating this catalyst in air for 3.5 hours at 150° C. led to the quantitative conversion of the mixed oxide species to Ag$_2$O, and recovery of catalytic activity. In the test procedure described previously the half-life for ozone decomposition at 16° C. was 3.8 minutes and 3.5 minutes in a second experiment run at 17° C., similar to the original performance of this catalyst.

The invention claimed is:

1. A catalyst for the destruction of ozone or hydrogen peroxide, comprising
    silver oxide and titania, wherein the silver oxide is present in an amount of at least 70% by weight of the catalyst, and further comprising MnO$_2$ in an amount of up to 10% by weight of the catalyst, and/or silica.

2. The catalyst according to claim 1, deposited onto a catalyst support.

3. The catalyst according to claim 2, wherein the catalyst support is a ceramic or metal flow-through monolith.

4. The catalyst according to claim 1, in the form of a pellet or shaped extrudate.

5. A method for removal of ozone or hydrogen peroxide from an atmosphere, comprising passing the atmosphere over the catalyst according to claim 1.

6. A method of sterilising an enclosed space, comprising humidifying the atmosphere in the space and subsequently or simultaneously supplying an effective amount of a sterilant comprising ozone or hydrogen peroxide that achieves sterilisation in a predetermined period, then subsequently catalytically destroying the sterilant by passing the atmosphere over the catalyst according to claim 1.

7. The method according to claim 6, further comprising regeneration of the catalyst.

8. The method according to claim 7, wherein the catalyst is regenerated by heating in air.

9. A catalyst for the destruction of ozone or hydrogen peroxide, consisting of silver oxide and titania, wherein the silver oxide is present in an amount of at least 70% by weight of the catalyst.

10. The catalyst according to claim 9, deposited onto a catalyst support.

11. The catalyst according to claim 10, wherein the catalyst support is a ceramic or metal flow-through monolith.

12. The catalyst according to claim 9, in the form of a pellet or shaped extrudate.

13. A method for removal of ozone or hydrogen peroxide from an atmosphere, comprising passing the atmosphere over the catalyst according to claim 9.

14. A method of sterilising an enclosed space, comprising humidifying the atmosphere in the space and subsequently or simultaneously supplying an effective amount of a sterilant comprising ozone or hydrogen peroxide that achieves sterilisation in a predetermined period, then subsequently catalytically destroying the sterilant by passing the atmosphere over the catalyst according to claim 9.

15. The method according to claim 14, further comprising regeneration of the catalyst.

16. The method according to claim 15, wherein the catalyst is regenerated by heating in air.

\* \* \* \* \*